US012643315B2

(12) United States Patent
Takehara et al.

(10) Patent No.: US 12,643,315 B2
(45) Date of Patent: Jun. 2, 2026

(54) X-RAY-TRANSMITTING MEMBER, X-RAY INSPECTION DEVICE, AND ARTICLE TO BE SUBJECTED TO X-RAY INSPECTION

(71) Applicant: TORAY INDUSTRIES, INC., Tokyo (JP)

(72) Inventors: Tomohiro Takehara, Iyo-gun (JP); Hidetoshi Sakai, Iyo-gun (JP)

(73) Assignee: TORAY INDUSTRIES, INC., Tokyo (JP)

( * ) Notice: Subject to any disclaimer, the term of this patent is extended or adjusted under 35 U.S.C. 154(b) by 104 days.

(21) Appl. No.: 18/724,880

(22) PCT Filed: Dec. 26, 2022

(86) PCT No.: PCT/JP2022/047883
§ 371 (c)(1),
(2) Date: Nov. 26, 2024

(87) PCT Pub. No.: WO2023/132287
PCT Pub. Date: Jul. 13, 2023

(65) Prior Publication Data
US 2025/0083427 A1     Mar. 13, 2025

(30) Foreign Application Priority Data
Jan. 5, 2022     (JP) ................................. 2022-000364

(51) Int. Cl.
*B32B 3/10*          (2006.01)
*A61B 6/04*          (2006.01)
(Continued)

(52) U.S. Cl.
CPC ............. *B32B 27/12* (2013.01); *A61B 6/0407* (2013.01); *B32B 5/145* (2013.01); *B32B 27/32* (2013.01);
(Continued)

(58) Field of Classification Search
None
See application file for complete search history.

(56) References Cited

U.S. PATENT DOCUMENTS

2013/0051535 A1     2/2013   Davis et al.
2018/0244879 A1     8/2018   Takehara et al.

FOREIGN PATENT DOCUMENTS

JP        2008207523  A  *  9/2008
JP        2012-42647   A      3/2012
(Continued)

OTHER PUBLICATIONS

Machine translation of JP-2016049649-A (Year: 2016).*
(Continued)

*Primary Examiner* — Christopher M Polley
(74) *Attorney, Agent, or Firm* — Birch, Stewart, Kolasch & Birch, LLP

(57) ABSTRACT

An X-ray transmission member including a substantially sheet-like X-ray transmitting part composed of a fiber-reinforced plastic containing discontinuous reinforcing fibers and a resin, the X-ray transmitting part having uneven thickness and a substantially uniform area weight. Provided is an X-ray transmission member made of a fiber-reinforced plastic, the member having a uniform radiolucency even if it has a shape whose thickness varies in the member plane.

15 Claims, 2 Drawing Sheets

(51) Int. Cl.

| | | |
|---|---|---|
| *B32B 5/14* | (2006.01) | |
| *B32B 27/12* | (2006.01) | |
| *B32B 27/32* | (2006.01) | |
| *B32B 37/10* | (2006.01) | |
| *G01N 23/04* | (2018.01) | |

(52) U.S. Cl.
CPC ............. *B32B 37/10* (2013.01); *G01N 23/04* (2013.01); *B32B 2250/05* (2013.01); *B32B 2262/106* (2013.01); *B32B 2307/40* (2013.01); *B32B 2307/7376* (2023.05); *B32B 2323/10* (2013.01); *B32B 2535/00* (2013.01)

(56) References Cited

FOREIGN PATENT DOCUMENTS

| | | | |
|---|---|---|---|
| JP | 2012-242381 A | | 12/2012 |
| JP | 2015-137876 A | | 7/2015 |
| JP | 2016-49649 A | | 4/2016 |
| JP | 2016049649 A | * | 4/2016 |
| JP | 2018-51000 A | | 4/2018 |

OTHER PUBLICATIONS

Machine translation of JP-2008207523-A (Year: 2008).*
International Search Report, issued in PCT/JP2022/047883, PCT/ISA/210, dated Feb. 7, 2023.
Written Opinion of the International Searching Authority, issued in PCT/JP2022/047883, PCT/ISA/237, dated Feb. 7, 2023.
Extended European Search Report for European Application No. 22918871.9, dated Oct. 31, 2025.

* cited by examiner

[Fig. 1]
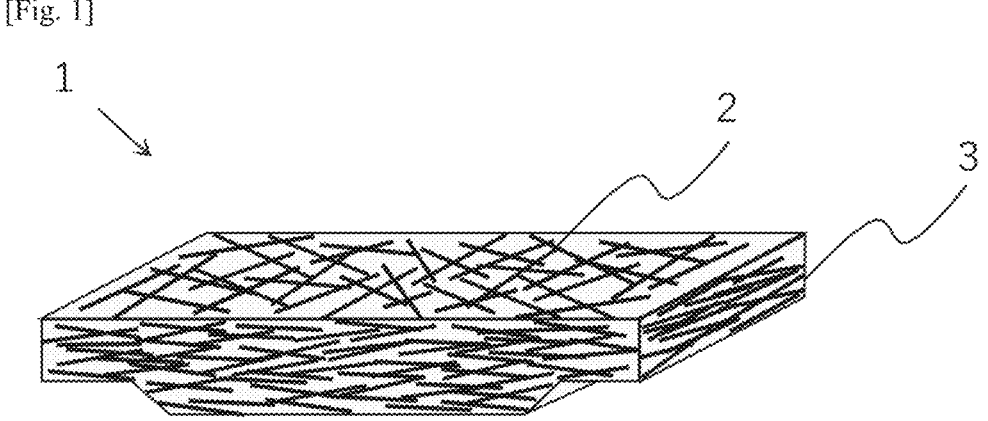
[Fig. 2]
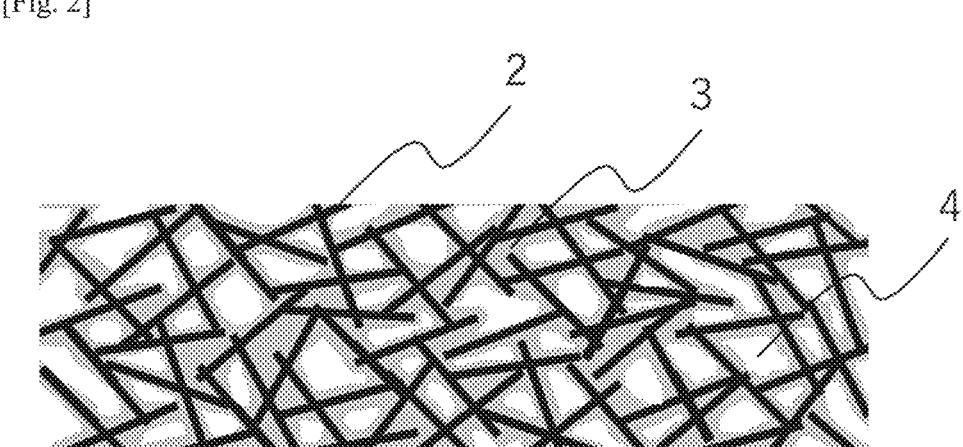

[Fig. 3]
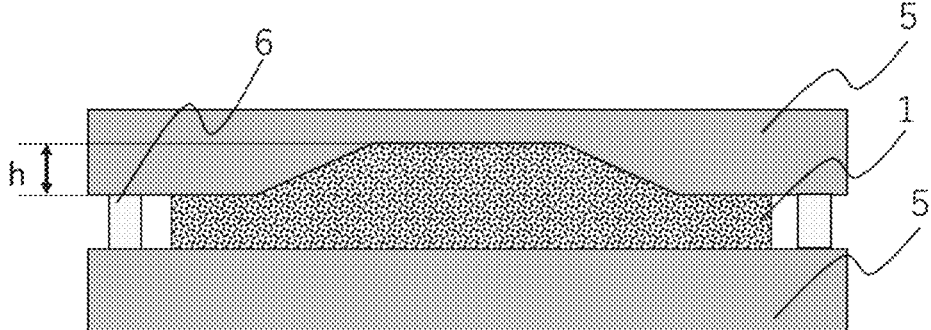
[Fig. 4]
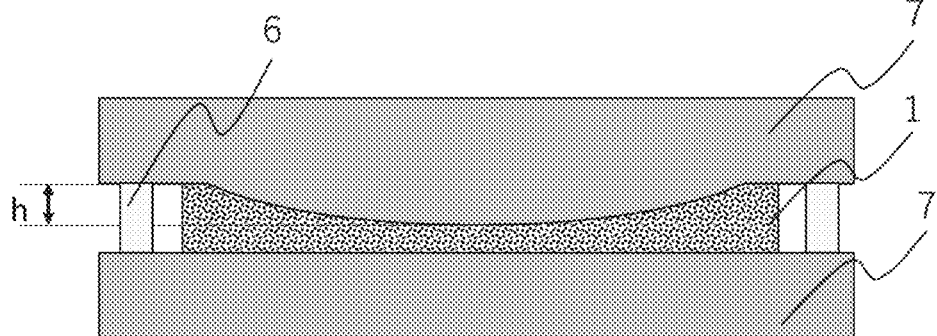

1

X-RAY-TRANSMITTING MEMBER, X-RAY INSPECTION DEVICE, AND ARTICLE TO BE SUBJECTED TO X-RAY INSPECTION

TECHNICAL FIELD

The present invention relates to an X-ray transmission member, X-ray inspection equipment, and an X-ray inspected product. More specifically, the present invention relates to an X-ray transmission member to be applied as a structural member of a pail through which X-rays penetrate; X-ray inspection equipment equipped with the X-ray transmission member, such as an imaging table on which an object is to be placed for imaging, or a housing of an X-ray cassette; and an X-ray inspected product having a housing to which the X-ray transmission member has been applied.

BACKGROUND ART

Imaging tables and housings of X-ray inspection equipment, for example, X-ray imaging equipment such as mammography equipment, X-ray cassettes, X-ray CT apparatuses, and IVR equipment, require materials with high radiolucency and high stiffness. Examples of such materials that have been conventionally applied include fiber-reinforced plastics, and sandwich structures in which a low-density resin foam core is sandwiched between skins composed of a fiber-reinforced plastic.

Further, since housings of X-ray inspected products to be subjected to industrial non-destructive testing require not only high strength and rigidity for the protection of integrated components, but also good radiolucency, fiber-reinforced plastics are applied to such housings in some cases.

Some imaging tables and housings of X-ray inspection equipment have a shape whose thickness varies in the member plane, in other words, a shape with uneven thickness, for the purpose of increasing the rigidity or equalizing the rate of radiolucency in cases where the angle of incidence of X-rays changes. In particular, in some cases, an imaging table of medical X-ray imaging equipment preferably has a shape with uneven thickness in which a curved surface shape is formed from the viewpoint of easily supporting a subject, and also from the viewpoint of designing. Further, in some cases, a housing of an X-ray inspected product employs a shape with uneven thickness in in which, for example, a thick part is formed from the viewpoint of designing and mechanical properties.

In cases where a fiber-reinforced plastic is processed to have uneven thickness, it is common to partially change the number of stacked prepregs. For example, Patent Document 1 discloses a technique in which, in a top board made of a fiber-reinforced plastic in an X-ray CT apparatus, a portion having a different thickness is partially formed in the transverse direction. The document describes that the number of stacked prepregs in a thick portion is increased in order to change the thickness of the top board.

Further, a common method of obtaining an X-ray transmission member having uneven thickness employs a sandwich structure in which a low-density resin foam core is sandwiched between skins composed of a fiber-reinforced plastic, wherein the resin foam has a shape with uneven thickness. For example, Patent Document 2 describes that, in a panel member for an X-ray cassette, a flat preform composed of uncured fiber-reinforced resin sheets (prepregs) that constitute the skin and a resin foam sheet having a homogeneous density and thickness is compression-molded using a mold with anon-flat surface, to compress and densify the resin foam sheet in a thin area.

PRIOR ART DOCUMENTS

Patent Documents

[Patent Document 1]JP 2018-51000 A
[Patent Document 2]JP 2008-207523 A

SUMMARY OF THE INVENTION

Problems to be Solved by the Invention

The top board described in Patent Document 1 achieves the uneven thickness by partially changing the number of stacked prepregs. Therefore, the radiolucency in an area with a larger number of stacked prepregs is lower than in an area with a smaller number of stacked prepregs. As a result, there have been cases where an uneven X-ray image was obtained or where an image of a thick portion appeared in the X-ray image even when the incident X-rays were perpendicular to the planar direction of the top board.

The panel described in Patent Document 2 achieves the uneven thickness by partially compressing and densifying the resin foam. However, in a resin foam having a low elastic modulus and low strength, application of a pressure during the compression molding relatively easily causes deformation in the in-plane direction. Therefore, in some cases, there have been limitations in the effect that enables achievement of a homogeneous rate of radiolucency in the member plane by suppressing variation of the weight per unit area.

In industrial non-destructive testing, absorption and scattering vary depending on the shape of the inspected product, so that highly accurate testing of the internal structure requires homogeneous radiolucency. Therefore, there have been limitations in achievement of high stiffness by introduction of a reinforcing structure having a different thickness such as a rib.

The present invention was made in view of the above problems, and an object of the present invention is to provide an X-ray transmission member made of a fiber-reinforced plastic, the member having uniform radiolucency even if it has a shape with uneven thickness wherein the thickness varies in the member plane.

Means for Solving the Problems

In order to solve the above problems, the present invention has the following constitution.

(1) An X-ray transmission member comprising a substantially sheet-like X-ray transmitting part composed of a fiber-reinforced plastic containing discontinuous reinforcing fibers and a resin, the X-ray transmitting part having uneven thickness and a substantially uniform area, weight.

(2) The X-ray transmission member according to (1), wherein
the X-ray transmitting part has a shape with uneven thickness including: a thick area that is 1.2 times to 5.0 times thicker than the thinnest portion; and a thin area that is less than 1.2 times thicker than the thinnest portion; and
the X-ray transmitting part satisfies $0.95 \leq W_1/W_2 \leq 10.05$, wherein $W_1$ is the average area weight of the thick area, and $W_2$ is the average area weight of the thin area.

(3) The X-ray transmission member according to (1) or (2), wherein the CV value of the area weight in the whole area of the X-ray transmitting part is not more than 5%.

(4) The X-ray transmission member according to (2), which satisfies $0.95 \leq X_1/X_2 \leq 1.05$, wherein $X_1$ is the average rate of radiolucency of the thick area, and $X_2$ is the average rate of radiolucency of the thin area.

(5) The X-ray transmission member according to any one of (1) to (4), wherein the CV value of the rate of radiolucency in the whole area of the X-ray transmitting part is not more than 5%.

(6) The X-ray transmission member according to any one of (1) to (5), wherein the rate of radiolucency as measured with RQA-M2, which is a radiation quality in accordance with IECO62220-L by a narrow beam system in accordance with IEC61331-1 is 85% to 98% at an arbitrary site(s) in the X-ray transmitting part.

(7) The X-ray transmission member according to any one of (1) to (6), wherein the fiber-reinforced plastic is a porous body in which voids are formed.

(8) The X-ray transmission member according to any one of (1) to (7), wherein the reinforcing fibers contained in the fiber-reinforced plastic have a ratio between the fiber length Lf and the fiber diameter d, Lf/d, of 100 to 8,000.

(9) The X-ray transmission member according to any one of (1) to (8), wherein the reinforcing fibers contained in the fiber-reinforced plastic include reinforcing fibers having an Lf/d value of more than 1,500 at 0 to 50% by weight, reinforcing fibers having an Lf/d value of 300 to 1,500 at 50 to 100% by weight, and reinforcing fibers having an L/d value of less than 300 at 0 to 50% by weight.

Lf Fiber length of the reinforcing fiber d: Diameter of the reinforcing fiber

(10) The X-ray transmission member according to any one of (1) to (9), wherein the fiber-reinforced plastic has a structure in which the discontinuous reinforcing fibers are dispersed in a substantially monofilament-like state, and in which the resin is present in intersecting portions of the reinforcing fibers.

(11) The X-ray transmission member according to any one of (1) to (10), wherein, when the X-ray transmitting part is projected on a plane perpendicular to an X-ray irradiation direction, the short side of the smallest circumscribed rectangle of the projected shape of the member is not less than 10 cm.

(12) The X-ray transmission member according to any one of (1) to (11), wherein the thinnest portion of the X-ray transmitting part has a thickness of 0.5 mm to 5.0 mm.

(13) The X-ray transmission member according to (2), which satisfies $0.1 \, S_1/S_0 \leq 0.9$, wherein $S_0$ is the projected area of the X-ray transmitting part, and $S_1$ is the projected area of the thick area.

(14) The X-ray transmission member according to (2), wherein in the X-ray transmitting part, the thick area and the thin area have a continuous surface to form a curved surface shape.

(15) The X-ray transmission member according to (14), wherein the curved surface shape has a radius of curvature of 2,000 to 12,000 mm.

(16) The X-ray transmission member according to (2), wherein the thick area has a rib shape.

(17) The X-ray transmission member according to any one of (1) to (16), further comprising a skin layer.

(18) X-ray inspection equipment comprising the X-ray transmission member according to any one of (1) to (17).

(19) An X-ray inspected product comprising a housing to which the X-ray transmission member according to any one of (1) to (17) has been applied Effect of the Invention The X-ray transmission member of the present invention can maintain uniform radiolucency while having uneven thickness. Therefore, for X-ray inspection equipment, and X-ray inspected products to be subjected to non-destructive testing, increased flexibility can be provided for shaping of, for example, an imaging table or a cassette housing, or a housing for containing the content of an inspected product, without deteriorating the image quality of the X-ray image.

BRIEF DESCRIPTION OF THE DRAWINGS

FIG. 1 is a schematic diagram illustrating an example of the X-ray transmission member of the present invention FIG. 2 is a schematic diagram illustrating an example of a cross-section of the X-ray transmission member of the present invention.

FIG. 3 is a schematic diagram illustrating a method of producing an X-ray transmission member in the Examples of the present invention.

FIG. 4 is a schematic diagram illustrating a method of producing an X-ray transmission member in the Examples of the present invention.

MODE FOR CARRYING OUT THE INVENTION

In the present description, the X-ray inspection equipment is typically a medical device that acquires an X-ray image of a human body, and examples of the X-ray inspection equipment mainly include mammography equipment, X-ray cassettes. X-ray CT apparatuses, and IVR equipment. However, the X-ray inspection equipment is not limited as long as it is equipment for testing the inside of a structure using X-rays. The X-ray inspection equipment is also includes industrial X-ray inspection equipment for use in non-destructive testing of an object. The X-ray inspected product subjected to the non-destructive testing is preferably an industrial product that routinely undergoes X-ray inspection prior to the product shipment. Examples of such an X-ray inspected product include products containing an internal circuit, wiring, or piping, such as rechargeable batteries, capacitors, and motors. The X-ray transmission member according to the present invention is a structural member that constitutes an area through which X-rays penetrate in such X-ray inspection equipment or an inspected product. Specific examples of the X-ray transmission member of the X-ray inspection equipment include a, member constituting a, housing for protecting an X-ray tube, a, housing for protecting a detector that detects X-rays to convert them into an image, a component member of an integrated component that eliminates scattering radiation, an imaging table that supports a subject in cases of a medical device, and an imaging table that supports an object in cases of industrial X-ray inspection equipment, or the like.

The X-ray transmission member of the present invention comprises a substantially sheet-like X-ray transmitting part composed of a fiber-reinforced plastic containing discontinuous reinforcing fibers and a resin. The term "substantially sheet-like" means a shape with a certain degree of flatness for which the thickness direction and the planar direction can be recognized. In the present invention, the X-ray transmitting part means an area where the incidence of radiated X-rays occurs in the X-ray transmission member. The overall shape of the X-ray transmission member is not limited as long as the X-ray transmitting part has a substantially sheet-like shape, and a standing wall or the like may be formed from the outer periphery of the X-ray transmitting part. The X-ray transmission member may be the imaging table or the housing itself, or may be a member constituting part of the imaging table or the housing. The thickness of the X-ray transmitting part in the present description means the thickness in the reference X-ray irradiation direction, in other words, the thickness in the X-ray irradiation direction in cases where the X-ray irradiation direction is constant for the X-ray inspection equipment and the X-ray inspected product subjected to the non-destructive testing to which the X-ray transmitting part is applied, or the thickness in the X-ray irradiation direction in the initial state in cases where the X-ray irradiation direction changes. For example, for an imaging table that is normally placed in parallel to the floor surface and irradiated with X-rays from directly above, the thickness of the X-ray transmitting part means the thickness in the direction perpendicular to the floor surface. The term "projected area of the X-ray transmitting part" is used to mean the projected area in the reference X-ray irradiation direction.

The type of the resin contained in the fiber-reinforced plastic is not limited, and either a thermosetting resin or a thermoplastic resin may be used. In the case of a thermosetting resin, the resin can be cured by the heat during molding, or when necessary, by additionally heating the resin after the molding to a temperature at which curing of the thermosetting resin occurs, to produce a matrix resin. In cases of a thermoplastic resin, the resin melted by the heat during molding is cooled and solidified to produce a matrix resin. The thermosetting resin is not limited as long as crosslinking reaction occurs by heat to at least partially form a three-dimensional crosslinking structure. Examples of the thermosetting resin include epoxy resins, vinyl ester resins, phenolic resins, and unsaturated polyester resins. As the molding substrate for the formation of the X-ray transmission member, it is preferred to use a prepreg prepared by impregnating reinforcing fibers with a thermosetting resin, especially preferably an epoxy resin, in a semi-cured state. Examples of the thermoplastic resin include polypropylene, polyethylene, polyamide, polyester, polyarylene sulfide, polyether ketone, polyether ether ketone, poly ether ketone ketone, polyether sulfone, polyimide, polyamide imide, polyether imide, and polysulfone. Examples of the thermoplastic resin also preferably include a cyclic oligomer as a precursor of any of these resins, and a resin prepared by mixing a plurality of these resins or their precursors. In particular, thermoplastic resins are preferred since, by the use of the resins, the later-mentioned attachment of the resin to the intersecting portions of the reinforcing fibers can be easily controlled to obtain a homogeneous structure. From the viewpoint of the radiolucency, it is especially preferred to use a polyolefin resin such as polypropylene or polyethylene having a low density.

The type of the reinforcing fibers is also not limited, and examples of the reinforcing fibers that may be used include inorganic fibers such as carbon fibers and glass fibers; organic fibers such as aramid fibers; and natural fibers. One of these types may be used, or two or more of these types may be used in combination. From the viewpoint of suppressing bending of the fibers, or suppressing variation of the area weight in the area with uneven thickness, carbon fibers such as PAN (polyacrylonitrile)-based or pitch-based carbon fibers are especially preferably used because of their high specific strength and specific rigidity. Further, from the viewpoint of the balance between the strength and the economy, it is also preferred to use carbon fibers and glass fibers in combination, or, from the viewpoint of the balance between the strength and the impact resistance, it is also preferred to use carbon fibers and organic fibers in combination, From the viewpoint of achieving homogeneous radiolucency and mechanical properties, it is more preferred to use only carbon fibers.

While the X-ray transmitting part of the X-ray transmission member of the present invention has a substantially sheet-like shape, it has a shape with uneven thickness wherein the thickness varies in the plane. The shape with uneven thickness is, for example, a shape having a thick center and a thin circumference as illustrated in FIG. 1. However, the arrangement of the thick area and the thin area is not limited to the arrangement illustrated in FIG. 1. The X-ray transmitting part preferably has a shape with uneven thickness including: a thick area that is 1,2 times to 5.0 times thicker than the thinnest portion; and a thin area that is less than 1.2 times thicker than the thinnest portion. The maximum thickness of the thick area is more preferably 1.2 times to 3.0 times the thickness of the thinnest portion. In cases where the thickness of the thick area is within this range, the effect of the present invention described above can be especially remarkably obtained.

The thickness of the thinnest portion of the X-ray transmitting part is preferably 0.5 mm to 5.0 nm. In cases where the thickness of the thinnest portion is within this range, the effect of the present invention described above can be especially remarkably obtained.

The X-ray transmitting part in the present invention has a substantially uniform area weight while having such uneven thickness. More specifically, the X-ray transmitting part preferably satisfies $0,95 \leq W_1/W_2 \leq 1.05$, wherein $W_1$ is the average area weight of the thick area, and $W_2$ is the average area weight of the thin area. In cases where the X-ray transmitting part has such a uniform area weight, in other words, in cases where the variation of the area weight is low, the variation of the X-ray absorptivity can be low. As a result, a homogeneous X-ray image can be obtained without allowing appearance of an image derived from uneven thickness. Therefore, in an X-ray transmission member, the uneven thickness can be utilized for the purpose of increasing the in-plane stiffness, or a curved surface shape can be given for the purpose of allowing the member to easily support a subject. This uniform area weight also enables improvement of the accuracy of X-ray inspection, more specifically, the diagnostic accuracy for identifying a lesion in cases of a medical device, or the testing accuracy for identifying an internal structure in cases of non-destructive testing of an object. The area weight means the weight per unit area. The $W_1/W_2$ described above more preferably satisfies $0.97 \leq W_2 \leq 1.03$, still more preferably satisfies $0.99 \leq W_1/W_2 \leq 1.01$.

The X-ray transmitting part in the present invention preferably satisfies $0.1 \leq S_1/S_0 \leq 0.9$, wherein $S_0$ is the projected area of the X-ray transmitting part, and $S_1$ is the projected area of the thick area. In cases where the ratio of the projected area of the thick area to the projected area of the X-ray transmitting part is within this range, flexibility in the design can be effectively achieved to allow, for example, improvement of the in-plane stiffness, or easier support of a subject.

Regarding the size of the X-ray transmitting part, when the X-ray transmission member is projected on a, plane perpendicular to an X-ray irradiation direction, the short side of the smallest circumscribed rectangle of the projected shape of the member is preferably not less than 10 cm. As described above in relation to the projected area, the X-ray irradiation direction herein means the reference X-ray irradiation direction. Since an X-ray transmission member of this preferred mode can maintain a substantially uniform area weight even in cases where the member is large, the size and the shape of the member are hardly limited, and high flexibility in the design can be achieved.

The CV value of the area weight of the entire X-ray transmitting part is preferably not more than 5%, more preferably not more than 3%. In the calculation of the CV value, the whole area of the X-ray transmitting part is divided into a grid of 3 cm×3 cm based on the projected area, and the area weight is calculated for the resulting samples. Based on the average and the standard deviation of the calculated area weight, the CV value is calculated. In the dividing into the grid, the samples are excised from around the centroid of the projected area of the entire X-ray transmitting part, and the remaining area in the edge of the X-ray transmitting part that cannot be excised into the above size is excluded from the measurement.

Area weight$[g/m^2]$=sample weight$[g]$/projected area $[m^2]$

CV value of the area weight$[\%]$=standard deviation of the area weight$[g/m^2]$/average area weight$[g/m^2]$×100

The X-ray transmitting part preferably satisfies $0.95 \leq X_1/X_2 \leq 1.05$, more preferably satisfies $0.97 \leq X_1/X_2 \leq 1.03$, still more preferably satisfies $0.99 \leq X_1/X_2 \leq 1.01$, wherein $X_1$ is the average rate of radiolucency of the thick area, and $X_2$ is the average rate of radiolucency of the thin area.

The CV value of the rate of radiolucency of the entire X-ray transmitting part is preferably not more than 5%, more preferably not more than 3%. The rate of radiolucency herein is a value derived from the ratio of a value detected in the state where X-rays penetrate the X-ray transmission member to a value detected without the X-ray transmission member, which is taken as 100. In the calculation of the CV value of the rate of radiolucency, the entire X-ray transmitting part is virtually divided into a grid of 3 cm×3 cm, and the rate of radiolucency is measured for a case where the irradiation is performed such that X-rays penetrate the center of each square of the grid. Based on the average and the standard deviation of the measured rate of radiolucency, the CV value is calculated. In the dividing into the grid, the samples are excised from around the centroid of the projected area of the entire X-ray transmitting part, and the remaining area in the edge of the X-ray transmitting part that cannot be excised into the above size is excluded from the measurement.

Rate of radiolucency$[\%]$=amount of X-ray penetrating the X-ray transmission member$[\mu Gy]$/ amount of X-ray without the X-ray transmission member$[\mu Gy]$×100

CV value of the rate of radiolucency$[\%]$=standard deviation of the rate of radiolucency$[\%]$/average rate of radiolucency$[\%]$×100

Under conditions with high X-ray radiant intensity, such as conditions at an X-ray tube voltage of not less than 60 kV or with a radiation quality of RQA-5 or the like, the X-ray penetrating power is high, so that a homogeneous X-ray image is likely to be obtained even in the presence of some degree of variation of the area weight due to uneven thickness. However, even under conditions with low X-ray radiant intensity, such as conditions with an X-ray tube voltage of less than 60 kV, or with a radiation quality of RQA-M2 or the like, the X-ray transmission member of the present invention enables acquisition of a homogeneous X-ray image without allowing appearance of an image derived from an area having uneven thickness. Thus, the X-ray transmission member of the present invention is suitably applicable to X-ray inspection equipment with an X-ray tube voltage of less than 60 kV in particular, mammography equipment.

The rate of radiolucency as measured with RQA-M2, which is a radiation quality in accordance with IEC62201-1, by a narrow beam system in accordance with IEC61331-1 is preferably 85% to 98% at an arbitrary site(s) in the X-ray transmitting part. In the calculation of the rate of radiolucency of the entire X-ray transmitting part, the thick area, or the thin area, the average and the standard deviation are preferably calculated from the rate of radiolucency measured after virtually dividing the part or area into a grid of 3 cm×3 cm as described above, However, more simply, the average and the standard deviation for arbitrary points (preferably not less than 5 points) in the entire X-ray transmitting part, the thick area, or the thin area may be used. Under such conditions with a high rate of radiolucency, an image derived from variation of the area weight or uneven thickness is especially likely to appear in the X-ray image, so that the effect of the present invention described above can be remarkably obtained.

The X-ray transmitting part is composed of a fiber-reinforced plastic containing discontinuous reinforcing fibers and a resin. Examples of the form of the discontinuous reinforcing fibers include a form in which the reinforcing fibers are in a bundle-like state, and a form in which the reinforcing fibers are opened to be in a substantially monofilament-like state. The term "substantially monofilament-like" herein means a fine-denier strand with less than 500 monofilaments of the discontinuous reinforcing fibers, and the term "bundle-like" means a strand with not less than 500 such monofilaments. Further, from the viewpoint of isotropy, which affects the shape quality regarding warping and the like of the X-ray transmission member, and from the viewpoint of the homogeneity of the X-ray image, the reinforcing fibers are preferably randomly dispersed in the in-plane direction.

As illustrated in FIG. 1, the fiber-reinforced plastic constituting the X-ray transmitting part preferably has a structure in which the discontinuous reinforcing fibers are dispersed in a substantially monofilament-like state, in which the resin is present in intersecting portions of the reinforcing fibers, and in which voids are formed as regions where neither the resin nor the reinforcing fibers are present. In other words, the fiber-reinforced plastic in the X-ray transmitting part is preferably a porous body in which voids are present. In cases where the fiber-reinforced plastic is such a porous body, a structure having higher mechanical properties than those of a simple resin foam can be obtained in terms of the elastic modulus, strength, and the like in the in-plane direction and the out-of-plane direction of the X-ray transmission member. Further, due to disturbance of the flow by the fibers, changes in the area weight can be suppressed even in cases where an area with uneven thickness is formed by partial pressing. Therefore, a homogeneous X-ray transmission member can be formed. The above fiber-reinforced plastic more preferably has a structure in which the reinforcing fibers are coated with the resin.

The discontinuous reinforcing fibers in the fiber-reinforced plastic constituting the X-ray transmitting part preferably have a ratio between the fiber length Lf and the fiber diameter d, Lf/d, of 100 to 8000. In cases where Lf/d is within the preferred range, the reinforcing effect by the discontinuous reinforcing fibers can be sufficiently obtained. On the other hand, the discontinuous reinforcing fibers hardly bend to increase intersections between the fibers, so that local formation of areas with increased area weight does not occur. Thus, the resulting X-ray image can have improved image quality since an excellent balance can be achieved between the homogeneity of arrangement of the discontinuous reinforcing fibers and the efficiency of reinforcement of the X-ray transmission member by the discontinuous reinforcing fibers.

From the viewpoint of the homogeneity of the resulting X-ray Image, the reinforcing fibers contained in the fiber-reinforced plastic constituting the X-ray transmitting part preferably include reinforcing fibers having an Lf/d value of more than 1500 at 0 to 50% by weight, reinforcing fibers having an Lf/d value of 300 to 1500 at 50 to 100% by weight, and reinforcing fibers having an Lf/d value of less than 300 at 0 to 50% by weight. The weight ratio of the reinforcing fibers herein is calculated relative to the total reinforcing fibers excluding the resin, which is taken as 100%.

In the measurement of the length Lf and the diameter d of the discontinuous reinforcing fibers, discontinuous reinforcing fibers are separated from the X-ray transmission member, and separated discontinuous reinforcing fibers are randomly extracted, followed by performing measurement based on their observation images obtained using an optical microscope or a scanning electron microscope. Examples of the method of separating the discontinuous reinforcing fibers from the X-ray transmission member include a method in which the resin of the X-ray transmission member is sufficiently dissolved using a solvent that dissolves the resin, and then extraction is carried out by a known operation such as filtration, and a method in which the resin is burned off by the burn-off method.

In the reinforcing fibers, the ratio between the length Ls and the distance between edges Ld (Ld/Ls) on a cross section is preferably 0.75 to 1.00. In cases where the ratio is within such a range, bending of the reinforcing fibers can be reduced, and the homogeneity in the X-ray penetration direction can be improved, resulting in improved homogeneity of the X-ray image obtained. The length Ls and the distance between edges Ld of the reinforcing fibers on a cross section herein are measured by a method in which a cross section perpendicular to the in-plane direction of the X-ray transmission member is analyzed from an observation image obtained using an optical microscope. The length Ls of a reinforcing fiber means the length of the fiber axis of the reinforcing fiber, and the distance between edges Ld means the length of the straight line connecting both edges of the reinforcing fiber. Since the measurement is carried out by the observation of the cross section, the depth direction cannot be taken into account. Therefore, the length Ls on the cross section and the fiber length Lf may be different from each other.

In the X-ray transmitting part, the average orientation angle of the reinforcing fibers in the direction perpendicular to the thickness direction is preferably 0° to 100°. In cases where the average orientation angle is within such a range, increases in the distance in the reinforcing fibers through which X-rays penetrate can be suppressed. Since this leads to favorable radiolucency, and improved homogeneity in the in-plane direction, the resulting X-ray image can have improved homogeneity, The orientation angle of a reinforcing fiber in the direction perpendicular to the thickness direction herein means an angle of the reinforcing fiber that is less than 90° formed with respect to the surface of the X-ray transmitting part. The orientation angle of a reinforcing fiber in the direction perpendicular to the thickness direction is measured by a method in which a cross section perpendicular to the in-plane direction of the X-ray transmission member is analyzed from an observation image obtained using an optical microscope.

The X-ray transmission member of the present invention preferably further comprises a skin layer on at least part of the surface of the X-ray transmitting part. By the presence of the skin layer, functionality can be imparted, for example, to improve durability such as the chemical resistance during washing and the weather resistance under the use environment, and to improve the scratch resistance against external force during the use or against abrasion caused by tools.

From the viewpoint of easily imparting such functionality, the skin layer is preferably a layer containing a thermoplastic resin as a major component. Examples of the type of the thermoplastic resin include polypropylene, polyethylene, polyamide, polyester polyarylene sulfide, polyether ketone, polyether ether ketone, polyether ketone, polyether sulfone, polyimide, polyamide imide, polyether imide, polysulfone, and fluororesin. Additives such as antibacterial agents and flame retardants may be added to these resins, and two or more of the resins may be mixed together. From the viewpoint of adhesion of the skin layer, the resin is preferably the same type of resin as the resin contained in the X-ray transmission member.

From the viewpoint of improving mechanical properties of the X-ray transmission member such as the strength and the elastic modulus, the skin is preferably a fiber-reinforced plastic. Examples of the type of the reinforcing fibers constituting the fiber-reinforced plastic of the skin layer include those exemplified for the discontinuous reinforcing fibers, From the viewpoint of efficiently producing the mechanical-property-improving effect, the reinforcing fibers constituting the fiber-reinforced plastic of the skin layer preferably have a longer fiber length than the discontinuous reinforcing fibers of the X-ray transmission member. The reinforcing fibers are more preferably continuous fibers in which fibers are present without cutting. Examples of the form of the continuous fibers include a form in which the fibers are unidirectionally aligned, and a woven fabric form in which fiber bundles are woven together. Examples of the type of the matrix resin constituting the skin that is the fiber-reinforced plastic include those exemplified as the resin contained in the X-ray transmission member.

The skin layer is preferably formed such that the layer covers at least the X-ray transmitting part. In cases where the skin layer is in such a mode, destruction of the X-ray transmission member due to scratches, dents, and the like can be suppressed when an external load or impact acts on the member. From the viewpoint of increasing the radiolucency by reducing the weight of the material through which X-rays penetrate, the X-ray transmission member preferably has a canape structure in which only one side of the member has a skin layer. From the viewpoint of protection against loads and impacts that act from the outside, and suppression of defects such as breakdown of integrated components due to interference with the integrated components, the X-ray transmission member preferably has a sandwich structure in which both sides of the member have skin layers.

Further, from the viewpoint of preventing reduction of the effect of the present invention, the skin layer is preferably a layer that covers the X-ray transmitting part at a uniform thickness, and the thickness is preferably not more than 500 μm. The density of the skin layer is preferably not more than 1.8 g/cm³. In cases where the skin layer is in such a mode, appearance of the skin layer in the X-ray image can be effectively suppressed.

In cases where the X-ray transmission member of the present invention is used for, for example, a top board of an imaging table of X-ray inspection equipment, a homogeneous X-ray image can be obtained even when the top board has a stepped shape such as embossing for labels indicating a test area or for placement or positioning of a subject. However, from the viewpoint of the homogeneity of the resulting X-ray image, the thick area and the thin area of the X-ray transmitting part preferably have a continuous surface to form a curved surface shape. The entire surface of the X-ray transmitting part especially preferably forms a curved surface shape having no steps. In cases where the X-ray transmission member is in such a mode, the subject can be easily supported while the homogeneity of the radiolucency is maintained. Therefore, slippage of the subject during the X-ray imaging can be suppressed to improve the image quality of the resulting X-ray image, The curved surface shape is preferably concave from the viewpoint of supporting the subject.

The curved surface shape preferably has a radius of curvature of 2,000 to 12,000 mm. In cases where the radius of curvature is within the preferred range, appearance of a relatively thick area in the X-ray image can be prevented while improvement of the in-plane stiffness and easiness of supporting the subject, obtained by employing the curved surface shape, can both be easily achieved.

In another mode of the X-ray transmission member of the present invention, the thick area of the X-ray transmitting part preferably has a rib shape. In cases where the thick area has a rib shape, the X-ray transmission member can have improved in-plane stiffness. The rib shape herein means a shape in the thick area in which the ratio between the length in the transverse direction $t_b$ and the length in the longitudinal direction $t_1(t_1/t_b)$ is not less than 10. More specifically, the rib shape is, for example, a shape having parallel ribs formed by parallel arrangement of a plurality of ribs, or a shape having grid ribs formed by arrangement of a plurality of ribs into the shape of a grid.

As methods of producing the X-ray transmission member of the present invention, known methods such as compression molding and autoclave molding may be used. From the viewpoint of reducing the cycle time of the production, compression molding is preferred. Examples of the production method by compression molding include a method comprising: providing a molding material containing a reinforcing fiber substrate composed of discontinuous reinforcing fibers impregnated with a resin; and heating and compressing the molding material in a two-sided mold in which an internal space corresponding to the molded body having uneven thickness is formed. In cases where the resin is a thermosetting resin, the heating and compression cause curing of the resin, to produce the X-ray transmission member. In cases where the resin is a thermoplastic resin, cooling after the heating and compression causes solidification of the resin, to produce the X-ray transmission member. Further, in order to improve the formability, a preheat operation of preheating the molding material may be carried out before the heating and compression by the two-sided mold.

Examples of the reinforcing fiber substrate include a discontinuous-reinforcing-fiber mat. In the mat, the reinforcing fibers are preferably opened to be in a substantially monofilament-like state, and randomly dispersed in the in-plane direction.

Examples of a method of forming the skin layer include a method in which the skin layer is placed on the molding material to allow its integration at the time of the heating and compression, a method in which the skin layer is integrated by a known method such as thermal welding or the use of an adhesive, and a method in which the skin layer is attached using a method such as vacuum molding or compressed air molding.

EXAMPLES

The present invention is described more concretely by way of Examples below. However, the scope of the present invention is not limited by these Examples.

[Materials]

<Carbon Fiber Mats>

Carbon Fiber Mat 1

A copolymer containing polyacrylonitrile as a major component was subjected to spinning, calcination treatment, and surface oxidation treatment. The resulting carbon fibers, composed of continuous carbon fibers with a total monofilament number of 24,000, were cut to a length of 6 mm using a cartridge cutter, to obtain chopped carbon fibers. Thereafter, a dispersion medium composed of water and a surfactant was prepared, and fed to a paper-making device. After adjusting the mass of the chopped carbon fibers such that a desired area weight was achieved, the chopped carbon fibers were fed to the dispersion medium, and the resulting mixture was stirred to obtain a slurry in which the carbon fibers were dispersed in a substantially monofilament-like state. Subsequently, the slurry was sucked from a water storage tank of the paper-making device, and then dehydrated, followed by drying in a hot air dryer at 150° C. for 2 hours, to obtain a carbon fiber mat with an area weight of 100 g/m².

Carbon Fiber Mat 2

A copolymer containing polyacrylonitrile as a major component was subjected to spinning, calcination treatment, and surface oxidation treatment. The resulting carbon fibers, composed of continuous carbon fibers with a total monofilament number of 24,000, were cut to a length of 9 mm using a cartridge cutter, to obtain chopped carbon fibers. The chopped carbon fibers were allowed to fall freely from a height of 80 cm, to obtain a carbon fiber mat with an area weight of 100 g/m² in which bundle-like chopped carbon fibers were randomly dispersed.

<Polypropylene (PP) Films>

PP Film 1

A polypropylene film with an area weight of 100 g/m² was prepared using a master batch prepared by mixing a polypropylene (unmodified polypropylene "Prime Polypro" (registered trademark) J106MG (manufactured by Prime Polymer Co., Ltd.)) at 90% by mass and an acid-modified polypropylene ("Admer" (registered trademark) QE800 (manufactured by Mitsui Chemicals, Inc.)) at 10% by mass.

PP Film 2

A polypropylene film with an area weight of 30 g/m² was prepared using a master batch prepared by mixing an acid-modified polypropylene (Umex 1010, manufactured by Sanyo Chemical Industries, Ltd.) at 30% by mass and a polypropylene (J229E, manufactured by Mitsui Chemicals, Inc.) at 70% by mass.

<Prepreg>

As a precursor of the fiber-reinforced plastic for forming the skin layer, "Toray ca (registered trademark) Prepreg" F6347B-05K, manufactured by Toray Industries, Inc. was used.

<Resin Foamn>

As a polypropylene resin foam sheet with a thickness of 3 nm and a bulk density of 330 kg/m³, "Efcell (registered trademark)" CP3030, manufactured by Furukawa Electric Co_, Ltd. was provided.

<CV Value of Area Weight>

The X-ray transmitting part in the X-ray transmission member prepared in each Example or Comparative Example, was excised to a size of 3 cm×3 cm based on the projected area. The excised sample was weighed to calculate the area weight. From the average and the standard deviation of the area weight, the CV value was calculated. In the dividing into the grid, samples were excised from around the centroid of the projected area of the entire X-ray transmitting part, and the remaining area in the edge of the X-ray transmitting part that could not be excised into the above size was excluded from the measurement.

$$CV \text{ value of the area weight}[\%] \text{standard deviation of the area weight}[g/m^2]/\text{average of the area weight}[g/m^2] \times 100$$

≤Ratio between Average Area Weight of Thick Area $W_1$ and Average Area Weight of Thin Area $W_2$: $W_1/W_2$>

Among the samples excised for the measurement of the CV value of the area weight, the samples corresponding to the thick area and the samples corresponding to the thin area were separately subjected to calculation of the average area weight to calculate $W_1$ and $W_2$, respectively. The samples including both the thick area and the thin area were excluded from the calculation.

<Rate of Radiolucency>

The X-ray transmitting part in the X-ray transmission member prepared in each Example or Comparative Example was virtually divided into a grid of 3 cm×3 cm based on the projected area, and the rate of radiolucency was measured by performing X-ray irradiation such that X-rays penetrate the center of each square of the grid. The amount of X-ray without the X-ray transmission member was also measured. The measurement of the amount of X-ray was carried out with RQA-M2, which is a radiation quality in accordance with IEC62220-1, by a narrow beam system in accordance with 1EC61331-1. The distance from the focus of X-ray tube to the detector was 800 mm, and the aperture was adjusted to become 20 mm×20 mm in front of the detector. The average of the measured values obtained as described above was calculated to determine the rate of radiolucency. In the dividing into the grid, samples were excised from around the centroid of the projected area of the entire X-ray transmitting part, and the remaining area in the edge of the X-ray transmitting part that could not be excised into the above size was excluded from the measurement, $$\text{Rate of radiolucency}[\%] \text{amount of X-ray penetrating the X-ray transmission member}[\mu Gy]/\text{amount of X-ray without the X-ray transmission member} [\mu Gy] \times 100$$

≤Ratio between Average Rate of Radiolucency of Thick Area $X_1$ and Average Rate of Radiolucency of Thin Area $X_2$:$X_1/X_2$>

Amona the squares of the virtual grid excised in the above measurement, the squares corresponding to the thick area and the squares corresponding to the thin area were separately subjected to calculation of the average rate of radiolucency to calculate $X_1$ and $X_2$, respectively. The squares including both the thick area and the thin area were excluded from the calculation.

<CV Value of Rate of Radiolucency>

From the average and the standard deviation of the rate of radiolucency obtained by the above measurement, the CV value was calculated.

$$CV \text{ value of the rate of radiolucency}[\%]=\text{standard deviation of the rate of radiolucency}[\%]/\text{average of the rate of radiolucency}[\%] \times 100$$

≤Ratio between Fiber Length Lf and Fiber Diameter d:Lf/d>

Samples excised from the X-ray transmitting part of the X-ray transmission member prepared in each Example or Comparative Example were heated in air at 500° C. for 1 hour to burn off the resin component. From around the center, 400 remaining reinforcing fibers were randomly selected, and the length Lf and the diameter d of each fiber were measured in the order of 1 μm using an optical microscope. The ratio between the fiber length Lf and the fiber diameter d was determined for each reinforcing fiber, and the resulting average was regarded as Lf/d.

<Mass Distribution of Fiber Length>

In the above measurement, reinforcing fibers having an Lf/d value of less than 300, reinforcing fibers having an Lf/d value of 300 to 1,500, and reinforcing fibers having an Lf/d value of more than 1,500 were collected into different groups, and the weight of the fibers in each group was measured, followed by calculating the weight ratio of each group.

<Evaluation of Image Quality of X-Ray Image>

For the X-ray transmission member prepared in each Example or Comparative Example, X-ray images were taken with RQA-M2 and RQA-5, which are radiation qualities in accordance with IEC62220-1. Each X-ray image obtained was visually observed. In cases where a shape derived from uneven thickness did not appear in the image, the image was rated as "good" while in cases where such a shape appeared in the image, the image was rated as "poor".

Example 1

Eight layers of PP Film 1 and four layers of Carbon Fiber Mat 1 were stacked in the order of "PP Film 1/Carbon Fiber Mat 1/PP Film 1/PP Film 1/Carbon Fiber Mat 1/PP Film 1/PP Film 1/Carbon Fiber Mat 1/PP Film 1/PP Film 1/Carbon Fiber Mat 1/PP Film 1", to obtain a laminate with a size of 300 mm×300 mm. Using a hydraulic press machine, the obtained laminate was heated and compressed at a temperature of 180° C. at a surface pressure of 3 MPa, to impregnate the carbon fiber mats with a polypropylene resin. Thereafter, the laminate was cooled while the applied pressure was maintained, to obtain a molding material. Subsequently, the obtained molding material was preheated in an oven that was set to 180° C. At this time, the molding material was found to be bulky due to expanding in the thickness direction. The preheated molding material was placed in a two-sided mold 5 having a non-flat shape in which the difference in the thickness between the thickest portion and the thinnest portion (uneven-thickness height), h, is 2.0 mm (FIG. 3). Further, spacers 6 of 1.2 mm were placed on the circumference of the mold, and the molding material was cooled by compression at a temperature of 50° C. at a surface pressure of 3 MPa, to obtain an X-ray transmission member. As shown in Table 1, with either the RQA-M2 radiation quality or the RQA-5 radiation quality, the X-ray transmission member did not cause appearance of a shape derived from uneven thickness in the X-ray image, indicating that X-ray images with excellent image quality could be obtained.

Example 2

A molding material was obtained by the same method as in Example 1 except that Carbon Fiber Mat 2 was used instead of Carbon Fiber Mat 1. Subsequently, the obtained molding material was preheated in an oven that was set to 180° C. At this time, the molding material was found to slightly expand in the thickness direction. The preheated molding material was placed in a two-sided mold 5 having a non-flat shape with an uneven-thickness height h of 0.8 mm (FIG. 3). Further, spacers 6 of 1.2 mm were placed on the circumference of the mold, and the molding material was cooled by compression at a temperature of 50° C. at a surface pressure of 3 MPa, to obtain an X-ray transmission member. As shown in Table 1, with either the RQA-M2 radiation quality or the RQA-5 radiation quality, the X-ray transmission member did not cause appearance of a shape derived from uneven thickness in the X-ray image, indicating that X-ray images with excellent image quality could be obtained.

Example 3

An X-ray transmission member was obtained by the same method as in Example 1 except that a two-sided mold 7 having a curved surface shape with an uneven-thickness height h of 1.5 mm was used (FIG. 4) and that spacers 6 of 3.0 mm were placed. As shown in Table 1, with either the RQA-M2 radiation quality or the RQA-5 radiation quality, the X-ray transmission member did not cause appearance of a shape derived from uneven thickness in the X-ray image, indicating that X-ray images with excellent image quality could be obtained.

Example 4

On the whole area of both surfaces of the X-ray transmission member obtained in Example 1L PP Film 2 and PP Film 1 were stacked in this order from the side of the X-ray transmission member surface, Subsequently, the obtained laminate was placed in the two-sided mold 5 having a non-flat shape used in Example 1, and spacers 6 of 1.4 mm were placed on the circumference of the mold. The laminate was then heated and compressed at a temperature of 160° C. at a surface pressure of 3 MPa for 10 minutes. Thereafter, the laminate was cooled while the pressure was maintained, to obtain an X-ray transmission member. As shown in Table 1, with either the RQA-M$^2$ radiation quality or the RQA-5 radiation quality, the X-ray transmission member did not cause appearance of a shape derived from uneven thickness in the X-ray image, indicating that X-ray images with excellent image quality could be obtained. Further, the X-ray transmission member had a smooth surface, and hence was capable of suppressing irritation of the skin upon the contact.

Example 5

On the whole area of both surfaces of the X-ray transmission member obtained in Example 3, PP Film 2 and the prepreg were stacked in this order from the side of the X-ray transmission member surface. Subsequently, the obtained laminate was placed in the two-sided mold 7 having a curved surface shape used in Example 3, and spacers 6 of 3.4 mm were placed on the circumference of the mold. The laminate was then heated and compressed at a temperature of 160° C. at a surface pressure of 3 MPa for 10 minutes. Thereafter, the laminate was cooled while the pressure was maintained, to obtain an X-ray transmission member. As shown in Table 1, with either the RQA-M2 radiation quality or the RQA-5 radiation quality, the X-ray transmission member did not cause appearance of a shape derived from uneven thickness in the X-ray image, indicating that X-ray images with excellent image quality could be obtained. Further, the X-ray transmission member had a smooth surface, and hence was capable of suppressing irritation of the skin upon the contact.

Example 61

Twenty-four layers of PP Film 1 and twelve layers of Carbon Fiber Mat 1 were stacked such that twelve combinations of "PP Film 1/Carbon Fiber Mat 1/PP Film 1" were sequentially layered, to obtain a laminate with a size of 300 mm×300 mm. Using a hydraulic press machine, the obtained laminate was heated and compressed at a temperature of 180° C. at a surface pressure of 3 MPa, to impregnate the carbon fiber mats with a polypropylene resin. Thereafter, the laminate was cooled while the applied pressure was maintained, to obtain a molding material. Subsequently, the obtained molding material was preheated in an oven that was set to 180° C. At this time, the molding material was found to be bulky due to expanding in the thickness direction. The preheated molding material was placed in a two-sided mold 5 having anon-flat shape in which the difference in the thickness between the thickest portion and the thinnest portion (uneven-thickness height), h, is 11.5 mm (FIG. 3). Further, spacers 6 of 5.5 mm were placed on the circumference of the mold, and the molding material was cooled by compression at a temperature of 50° C. at a surface pressure of 3 MPa, to obtain an X-ray transmission member. As shown in Table 1, with the RQA-5 radiation quality, the X-ray transmission member did not cause appearance of a shape derived from uneven thickness in the X-ray image, indicating that an X-ray image with excellent image quality could be obtained. In contrast, when the radiation quality was RQA-M2, a shape derived from uneven thickness appeared in the X-ray image, so that the image quality of the X-ray image was rated as poor.

Comparative Example 1

A stack of "prepreg/polypropylene resin foam sheet/prepreg" in this order was prepared to obtain a laminate with a size of 300 mm×300 mm. The obtained laminate was placed in the two-sided mold 5 having a non-flat shape used in Example 1, and spacers 6 of 1.4 mm were placed on the circumference of the mold. The laminate was then heated and compressed at a temperature of 130° C. at a surface pressure of 2 MPa for 60 minutes, to allow curing of the prepreg. Thereafter, the laminate was demolded to obtain an X-ray transmission member. As shown in Table 1, with either the XRQA-M2 radiation quality and the RQA-5 radiation quality, the X-ray transmission member caused appearance of a shape derived from uneven thickness in the X-ray image so that the image qualities of the X-ray images were rated as poor.

TABLE 1

| | Example 1 | Example 2 | Example 3 | Example 4 | Example 5 | Example 6 | Comparative Example 1 |
|---|---|---|---|---|---|---|---|
| Maximum thickness of X-ray transmitting Part [mm] | 3.2 | 2.0 | 3.0 | 3.4 | 3.4 | 17.0 | 3.4 |
| Minimum thickness of X-ray transmitting Part [mm] | 1.2 | 1.2 | 1.5 | 1.4 | 1.9 | 5.5 | 1.4 |
| Ratio of average area weight of the thick area W1 and average area weight of the thin area W2:W1/W2 | 0.97 | 1.05 | 0.98 | 1.03 | 1.05 | 1.02 | 1.15 |
| CV Value of the area weight [%] | 3.8 | 4.3 | 2.2 | 4.5 | 3.9 | 4.6 | 6.1 |
| Rate of radiolucency [Note 1)] [%] | 93.8 | 93.4 | 94.1 | 93.2 | 92.4 | 84.2 | 94.7 |
| $X_1/X_2$ | 0.98 | 1.08 | 0.98 | 1.02 | 1.04 | 1.05 | 1.13 |
| CV value of the rate of radiolucency [%] | 4.2 | 4.9 | 2.4 | 4.8 | 4.3 | 4.9 | 7.0 |
| Whether fiber-reinforced plastic is a porous body in which voids are formed [Note 2)] | ○ | ○ | ○ | ○ | ○ | ○ | × |
| Ratio between fiber length Lf and fiber diameter d:Lf/d | 700 | 1,200 | 750 | 700 | 750 | 700 | — |
| Mass distribution of Lf/d [wt %]    Lf/d: less than 300 | 4 | 2 | 3 | 4 | 3 | 4 | — |
|     Lf/d: 300 to 1,500 | 94 | 82 | 95 | 94 | 95 | 94 | — |
|     Lf/d: more than 1,500 | 2 | 16 | 2 | 2 | 2 | 2 | — |
| Presence or Absence of fiber-reinforced plastic structure in which discontinuous reinforcing fibers are dispersed in substantially monofilament-like state and in which the resin is present in intersecting portions of the reinforcing fibers | present | absent | present | present | present | present | absent |
| Short side of the smallest circumscribed rectangle of the projected shape of the member [Note 3)] [cm] | 30 | 30 | 30 | 30 | 30 | 30 | 30 |
| Thickness of the thinnest part [mm] | 1.2 | 1.2 | 1.5 | 1.4 | 1.9 | 5.5 | 1.4 |
| $S_1/S_0$ | 0.65 | 0.25 | 0.33 | 0.65 | 0.33 | 0.65 | 0.25 |
| Whether the thick area and the thin area surface have a continuous surface to form a curved surface shape [Note 4)] | — | — | ○ | — | ○ | — | — |
| Radius of curvature of the curved surface shape [mm] | — | — | 3300 | — | 3300 | — | — |
| Shape of thick area | rib | rib | curve | rib | curve | rib | rib |
| Presence or Absence of skin layer | absent | absent | absent | present | present | absent | present |
| Image quality of X-ray image   RQA-M2 | good | good | good | good | good | Poor | Poor |
|    RQA-5 | good | good | good | good | good | good | Poor |

Note 1)

Rate of radiolucency as measured with RQA-M2, which is a radiation quality in accordance with IEC62220-1, by a narrow beam system in accordance with IEC61331-1, at arbitrary site(s) in the X-ray transmitting Part;

Note 2)

O: Yes, x: No;

Note 3)

Short side of the smallst circumscribed rectangle of the projected shape of the member, when the X-ray transmitting part is projected on a plane perpendicular to an X-ray irradiation direction;

Note 4)

○: Yes, x: No, —: Absence of curved surface shape

DESCRIPTION OF SYMBOLS

1. X-ray transmission member
2. Discontinuous reinforcing fiber
3. Resin
4. Void
5. Two-sided mold having a non-flat shape
6. Spacer
7. Two-sided mold having a curved surface shape
h. Uneven-thickness height

The invention claimed is:

1. An X-ray transmission member comprising a substantially sheet-like X-ray transmitting part composed of a fiber-reinforced plastic containing discontinuous reinforcing fibers and a resin, the X-ray transmitting part having uneven thickness and a substantially uniform area weight, wherein the coefficient of variation (CV) value of the area weight in the whole area of the X-ray transmitting part is not more than 5%, wherein the CV value of the rate of radiolucency in the whole area of the X-ray transmitting part is not more than 5%, wherein the fiber-reinforced plastic is a porous body in which voids are formed, and wherein the X-ray transmission member further comprises a skin layer.

2. The X-ray transmission member according to claim 1, wherein the X-ray transmitting part has a shape with uneven thickness including: a thick area that is 1.2 times to 5.0 times thicker than the thinnest portion; and a thin area that is less than 1.2 times thicker than the thinnest portion; and the X-ray transmitting part satisfies $0.95 \leq W_1/W_2 \leq 1.05$, wherein $W_1$ is the average area weight of the thick area, and $W_2$ is the average area weight of the thin area.

3. The X-ray transmission member according to claim 2, which satisfies $0.95 \leq X_1/X_2 \leq 1.05$, wherein $X_1$ is the average rate of radiolucency of the thick area, and $X_2$ is the average rate of radiolucency of the thin area.

4. The X-ray transmission member according to claim 1, wherein the rate of radiolucency as measured with RQA-M2, which is a radiation quality in accordance with IEC62220-1, by a narrow beam system in accordance with IEC61331-1 is 85% to 98% at an arbitrary site(s) in the X-ray transmitting part.

5. The X-ray transmission member according to claim 1, wherein the reinforcing fibers contained in the fiber-reinforced plastic have a ratio between the fiber length Lf and the fiber diameter d, Lf/d, of 100 to 8000.

6. The X-ray transmission member according to claim 1, wherein the reinforcing fibers contained in the fiber-reinforced plastic include reinforcing fibers having an Lf/d value of more than 1,500 at 0 to 50% by weight, reinforcing fibers having an Lf/d value of 300 to 1,500 at 50 to 100% by weight, and reinforcing fibers having an Lf/d value of less than 300 at 0 to 50% by weight, wherein:

Lf: Fiber length of the reinforcing fiber d: Diameter of the reinforcing fiber.

7. The X-ray transmission member according to claim 1, wherein the fiber-reinforced plastic has a structure in which the discontinuous reinforcing fibers are dispersed in a substantially monofilament-like state, and in which the resin is present in intersecting portions of the reinforcing fibers.

8. The X-ray transmission member according to claim 1, wherein, when the X-ray transmitting part is projected on a plane perpendicular to an X-ray irradiation direction, the short side of the smallest circumscribed rectangle of the projected shape of the member is not less than 10 cm.

9. The X-ray transmission member according to claim 1, wherein the thinnest portion of the X-ray transmitting part has a thickness of 0.5 mm to 5.0 mm.

10. The X-ray transmission member according to claim 2, which satisfies $0.1 \leq S_1/S_0 \leq 0.9$, wherein $S_0$ is the projected area of the X-ray transmitting part, and $S_1$ is the projected area of the thick area.

11. The X-ray transmission member according to claim 2, wherein in the X-ray transmitting part, the thick area and the thin area have a continuous surface to form a curved surface shape.

12. The X-ray transmission member according to claim 11, wherein the curved surface shape has a radius of curvature of 2,000 to 12,000 mm.

13. The X-ray transmission member according to claim 2, wherein the thick area has a rib shape.

14. X-ray inspection equipment comprising the X-ray transmission member according to claim 1.

15. An X-ray inspected product comprising a housing to which the X-ray transmission member according to claim 1 has been applied.

* * * * *